(12) United States Patent
Tennican

(10) Patent No.: US 10,207,098 B2
(45) Date of Patent: Feb. 19, 2019

(54) CATHETER DEVICES AND TECHNIQUES

(71) Applicant: Hyprotek, Inc., Spokane, WA (US)

(72) Inventor: Patrick O. Tennican, Spokane, WA (US)

(73) Assignee: Hyprotek, Inc., Spokane, WA (US)

( * ) Notice: Subject to any disclaimer, the term of this patent is extended or adjusted under 35 U.S.C. 154(b) by 632 days.

(21) Appl. No.: 13/688,073

(22) Filed: Nov. 28, 2012

(65) Prior Publication Data

US 2013/0138083 A1    May 30, 2013

Related U.S. Application Data

(60) Provisional application No. 61/564,206, filed on Nov. 28, 2011.

(51) Int. Cl.
*A61M 27/00* (2006.01)
*A61M 39/16* (2006.01)
(Continued)

(52) U.S. Cl.
CPC .......... *A61M 39/162* (2013.01); *A01N 59/00* (2013.01); *A61K 33/40* (2013.01); *A61M 11/08* (2013.01); *A61M 15/08* (2013.01); *A61M 25/002* (2013.01); *A61M 25/0017* (2013.01); *A61M 39/20* (2013.01); *A61K 9/0014* (2013.01); *A61K 47/183* (2013.01); *A61M 35/00* (2013.01); *A61M 39/165* (2013.01); *A61M 2025/0019* (2013.01); *A61M 2205/583* (2013.01); *A61M 2209/06* (2013.01); *F04C 2270/0421* (2013.01); *Y10S 604/905* (2013.01)

(58) Field of Classification Search
CPC .. A61M 39/20; A61M 39/162; A61M 39/165; A61M 2025/0019; A61M 2209/06; A61M 11/08; A61M 25/0017; A61M 25/002; A61M 35/00; A61M 2205/0019; A61M 2205/583; A01N 59/00; A61K 33/40; A61K 9/0014; A61K 47/183; F04C 2270/0421; A61B 19/34; Y10S 604/905
USPC ........ 604/246, 263, 533, 544; 206/210, 364, 206/571; 15/97.1; 134/6
See application file for complete search history.

(56) References Cited

U.S. PATENT DOCUMENTS

| 3,648,704 | A |   | 3/1972 | Jackson |         |
|-----------|---|---|--------|---------|---------|
| 3,967,728 | A | * | 7/1976 | Gordon et al. | 206/364 |

(Continued)

FOREIGN PATENT DOCUMENTS

| CN | 1717261 | 1/2006 |
| CN | 1806746 | 7/2006 |

(Continued)

OTHER PUBLICATIONS

The PCT Search Report dated Apr. 1, 2013 for PCT application No. PCT/US12/66886, 13 pages.

(Continued)

*Primary Examiner* — Andrew J Mensh
(74) *Attorney, Agent, or Firm* — Lee & Hayes, P.C.

(57) ABSTRACT

This application describes example antimicrobial compositions that may be used alone or in combination with catheters and catheter insertion sites. According to another aspect, the application describes catheters which may employ one or more protection devices, such as cleaning caps, protective caps or both.

20 Claims, 3 Drawing Sheets

(51) Int. Cl.

| | | |
|---|---|---|
| *A01N 59/00* | (2006.01) | |
| *A61M 11/08* | (2006.01) | |
| *A61M 15/08* | (2006.01) | |
| *A61M 39/20* | (2006.01) | |
| *A61K 33/40* | (2006.01) | |
| *A61M 1/00* | (2006.01) | |
| *B65D 81/24* | (2006.01) | |
| *B08B 7/00* | (2006.01) | |
| *A61M 25/00* | (2006.01) | |
| *A61M 35/00* | (2006.01) | |
| *A61K 9/00* | (2006.01) | |
| *A61K 47/18* | (2017.01) | |

(56) References Cited

U.S. PATENT DOCUMENTS

| | | | |
|---|---|---|---|
| 4,334,551 A | | 6/1982 | Pfister |
| 4,360,020 A | | 11/1982 | Hitchcock, Jr. et al. |
| 4,811,847 A | * | 3/1989 | Reif .................. A61M 25/002 206/210 |
| 5,048,684 A | | 9/1991 | Scott |
| 5,226,530 A | * | 7/1993 | Golden ................. 206/210 |
| 6,090,075 A | * | 7/2000 | House .............. A61M 25/0017 604/172 |
| 7,780,794 B2 | * | 8/2010 | Rogers et al. .................... 134/6 |
| 7,981,090 B2 | | 7/2011 | Plishka et al. |
| 8,336,152 B2 | | 12/2012 | Vaillancourt et al. |
| 2001/0001443 A1 | | 5/2001 | Kayerod et al. |
| 2003/0018322 A1 | * | 1/2003 | Tanghoj et al. .............. 604/544 |
| 2005/0265773 A1 | | 12/2005 | De Laforcade |
| 2006/0142737 A1 | * | 6/2006 | Tanghoj ........................ 604/544 |
| 2007/0161949 A1 | * | 7/2007 | Knox et al. ................. 604/93.01 |
| 2007/0213645 A1 | * | 9/2007 | Zumeris et al. ................. 601/46 |
| 2007/0282280 A1 | * | 12/2007 | Tennican ...................... 604/246 |
| 2008/0019889 A1 | | 1/2008 | Rogers et al. |
| 2008/0033371 A1 | | 2/2008 | Updegraff et al. |
| 2008/0132880 A1 | | 6/2008 | Buchman |
| 2009/0024111 A1 | * | 1/2009 | Borodulin et al. ........... 604/544 |
| 2009/0028750 A1 | | 1/2009 | Ryan |
| 2009/0299334 A1 | | 12/2009 | Nishtala et al. |
| 2009/0324508 A1 | | 12/2009 | Bobbert |
| 2010/0242993 A1 | * | 9/2010 | Hoang et al. ..................... 134/6 |
| 2011/0030726 A1 | | 2/2011 | Vaillancourt et al. |
| 2011/0052664 A1 | | 3/2011 | Tennican et al. |
| 2011/0064512 A1 | | 3/2011 | Shaw et al. |
| 2011/0171280 A1 | | 7/2011 | Toreki et al. |
| 2011/0201692 A1 | | 8/2011 | Raad |
| 2011/0301553 A1 | * | 12/2011 | Goral et al. .................. 604/265 |
| 2013/0030414 A1 | | 1/2013 | Gardner et al. |
| 2013/0138085 A1 | | 5/2013 | Tennican |

FOREIGN PATENT DOCUMENTS

| | | |
|---|---|---|
| CN | 101306221 | 11/2008 |
| CN | 101405042 | 4/2009 |
| CN | 101618384 | 1/2010 |
| CN | 101878050 | 11/2010 |
| DE | 29608617 | 8/1996 |
| JP | 2000153876 | 6/2000 |
| JP | 2003261177 | 9/2003 |
| JP | 2007089599 | 4/2007 |
| JP | 2000056273 | 3/2009 |
| JP | 2009537250 | 10/2009 |
| JP | 2013503713 | 2/2013 |
| JP | 2013518056 | 5/2013 |
| KR | 20090003267 | 1/2009 |
| WO | WO2000025846 | 5/2000 |
| WO | WO0165939 | 9/2001 |
| WO | WO2003064279 | 8/2003 |
| WO | WO2006071781 | 7/2006 |
| WO | WO2007137056 | 11/2007 |
| WO | WO2009076718 | 6/2009 |
| WO | WO2010002757 | 1/2010 |
| WO | WO2011022601 | 2/2011 |
| WO | WO2011028965 | 3/2011 |
| WO | WO2011053924 | 5/2011 |
| WO | WO2011091322 | 7/2011 |
| WO | WO02011109393 | 9/2011 |
| WO | WO2012067778 A1 | 5/2012 |

OTHER PUBLICATIONS

The PCT Search Report dated Feb. 26, 2013 for PCT application No. PCT/US12/66894, 11 pages.

The PCT Search Report dated Mar. 4, 2013 for PCT application No. PCT/US12/66880, 12 pages.

Hooton et al, "Diagnosis, Prevention, and Treatment of Catheter-Associated Urinary Tract Infection in Adults: 2009 Intl Clinical Practice Guidelines from the Infectious Disease Society of America", Mar. 2010, Urinary Catheter Guidelines, Clinical Infectious Diseases, vol. 50, 39 pgs.

Office Action for U.S. Appl. No. 13/688,078, dated Aug. 13, 2015, Patrick O. Tennican, "Antimicrobial Composition Including a Residual Barrier Film", 14 pages.

Office Action for U.S. Appl. No. 13/688,044, dated Aug. 19, 2016, Tennican, "Port and Surface Cleaning Devices and Techniques", 9 pages.

Office Action for U.S. Appl. No. 13/688,078, dated Sep. 9, 2016, Tennican, "Antimicrobial Composition Including a Residual Barrier Film", 9 pages.

Australian Office Action dated Oct. 14, 2016 for Australian Patent Application No. 2012346030, a counterpart foreign application of U.S. Appl. No. 13/688,073, 4 pages.

Austrlian Office Action dated Oct. 25, 2016 for Australian Patent Application No. 2012346036, a counterpart foreign application of U.S. Appl. No. 13/688,044, 3 pages.

Australian Office Action dated Oct. 7, 2015 for Australian patent application No. 2012346043, a counterpart foreign application of U.S. Appl. No. 13/688,044, 3 pages.

Australian Office Action dated Nov. 26, 2015 for Australian patent application No. 2012346043, a counterpart foreign application of U.S. Appl. No. 13/688,044, 3 pages.

Austrlian Office Action dated Jul. 11, 2016 for Australian patent application No. 2012346036, a counterpart foreign application of U.S. Appl. No. 13/688,044, 4 pages.

Australian Office Action dated Jul. 19, 2016 for Australian Patent Application No. 2012346043, a counterpart foreign application of U.S. Appl. No. 13/688,044, 3 pages.

Australian Office Action dated Jul. 31, 2017 for Australian Patent Application No. 2012346030, a counterpart foreign application of U.S. Appl. No. 13/688,073, 8 pages.

Australian Office Action dated Sep. 28, 2017 for Australian Patent Application No. 2012346030, counterpart foreign application of U.S. Appl. No. 13/688,073, 6 pages.

Chinese Office Action dated Jan. 23, 2017 for Chinese Patent Application No. 201280058307.6, a counterpart foreign application of U.S. Appl. No. 13/688,044, 15 pages.

Chinese Office Action dated Oct. 25, 2016 for Chinese Patent Application No. 201280058237.4, a counterpart foreign application of U.S. Appl. No. 13/688,044, 17 pages.

Chinese Office Action dated Nov. 13, 2015 for Chinese patent application No. 201280058237.4, a counterpart foreign application of U.S. Appl. No. 13/688,044, 18 pages.

Chinese Office Action dated Nov. 7, 2017 for Chinese patent application No. 201280058307.6, a counterpart foreign application of U.S. Appl. No. 13/688,073, 11 pages.

Chinese Office Action dated Feb. 14, 2016 for Chinese patent application No. 201280058307.6, a counterpart foreign application of U.S. Appl. No. 13/688,044, 16 pages.

Chinese Office Action dated Feb. 6, 2016 for Chinese patent application No. 201280058316.5, a counterpart foreign application of U.S. Appl. No. 13/688,044, 29 pages.

Chinese Office Action dated Apr. 28, 2017 for Chinese patent application No. 201280058316.5, a counterpart foreign application of U.S. Appl. No. 13/688,044, 20 pages.

(56) References Cited

OTHER PUBLICATIONS

Chinese Office Action dateed May 11, 2016 for Chinese patent application No. 201280058316.5, a counterpart foreign applicaton of U.S. Appl. No. 13/688,044, 28 pages.

Chinese Office Action dated May 5, 2016 for Chinese Patent Application No. 201280058237.4, a counterpart foreign application of U.S. Appl. No. 13/688,044, 18 pages.

Chinese Office Action dated Jul. 4, 2016 for Chinese patent application No. 201280058307.6, counterpart foreign application of U.S. Appl. No. 13/688,044, 15 pages.

Chinese Appeal decision dated Aug. 18, 2017 for Chinese patent application No. 201280058316.5, a counterpart foreign application of U.S. Appl. No. 13/688,044.

Chinese Office Action dated Aug. 28, 2015 for Chinese patent application No. 201280058307.6, a counterpart foreign application of U.S. Appl. No. 13/688,044, 16 pages.

Chinese Office Action dated Sep. 14, 2015 for Chinese patent application No. 201280058316.5, a counterpart foreign application of U.S. Appl. No. 13/688,044, 22 pages.

Chinese Office Action dated Sep. 28, 2016 for Chinese patent application No. 201280058316.5, a counterpart foreign application of U.S. Appl. No. 13/688,044, 24 pages.

European Office Action dated Sep. 25, 2015 for European patent application No. 12853916.0, a counterpart foreign Appl. of U.S. Appl. No. 13/688,044, 3 pages.

European Office Action dated Sep. 25, 2015 for European patent application No. 12852866.8, a counterpart foreign application of U.S. Appl. No. 13/688,078, 3 pages.

European Office Action dated Sep. 25, 2015 for European patent application No. 12852889.0, a counterpart foreign application of U.S. Appl. No. 13/688,073, 3 pages.

European Office Action dated Sep. 8, 2016 for European Patent Application No. 12852866.8, a counterpart foreign application of U.S. Appl. No. 13/688,078, 4 pages.

European Office Action dated Oct. 25, 2016 for European Patent Application No. 12852889.0, a counterpart foreign application of U.S. Appl. No. 13/688,073, 4 pages.

Extended European Search Report dated Jan. 14, 2016 for European Patent Application No. 12852889.0, 9 pages.

Extended European Search Report dated Jan. 7, 2016 for European Patent Application No. 12852866.8, 8 pages.

Extended European Search Report dated Jan. 7, 2016 for European patent application No. 12853916.0, 9 pages.

Japanese Office Action dated Jan. 24, 2017 for Japanese Patent Application No. 2014-543631, a counterpart foreign application of U.S. Appl. No. 13/688,078, 4 pages.

Japanese Office Action dated Dec. 25, 2017 for Japanese Patent Application No. 2014-543627, a counterpart foreign application of U.S. Appl. No. 13/688,073.

Japanese Office Action dated Jun. 13, 2017 for Japanese Patent Application No. 2014-543627, a counterpart foreign applicaton of U.S. Appl. No. 13/688,073, 10 pages.

Japanese Office Action dated Jun. 27, 2017 for Japanese Patent Application No. 2014-543628, a counterpart foreign application of U.S. Appl. No. 13/688,044, 9 pages.

Japanese Office Action dated of Sep. 20, 2016 for Japanese Patent Application No. 2014-543628, a counterpart foreign application of U.S. Appl. No. 13/688,044, 13 pages.

Japanese Office Action dated Sep. 20, 2016 for Japanese Patent Application No. 2014-543627, a counterpart foreign application of U.S. Appl. No. 13/688,073, 13 pages.

Japanese Office Action dated Oct. 4, 2016 for Japanese Patent Application No. 2014-543631, a counterpart foreign application for U.S. Appl. No. 13/688,078, 13 pages.

Japanese Office Action dated Dec. 19, 2017 for Japanese patent application No. 2014-543628, a counterpart foreign application for U.S. Appl. No. 13/688,044.

Mexican Office Action dated Oct. 9, 2017 for Mexican patent application No. MX/a/2014/006413, a counterpart foreign application of U.S. Appl. No. 13/688,044.

Office action for U.S. Appl. No. 13/688,044, dated Jan. 12, 2017, Tennican, "Port and Surface Cleaning Devices and Techniques", 8 pages.

Final Office Action for U.S. Appl. No. 13/688,044, dated Oct. 30, 2015, Patrick O. Tennican, "Port and Surface Cleaning Devices and Techniques", 10 pages.

Office action for U.S. Appl. No. 13/688,078, dated Nov. 8, 2017, Tennican, "Antimicrobial Composition Including a Residual Barrier Film", 11 pages.

Office action for U.S. Appl. No. 13/688,044, dated Dec. 20, 2017, Tennican, "Port and Surface Cleaning Devices and Techniques", 12 pages.

Office action for U.S. Appl. No. 13/688,078, dated Feb. 28, 2017, Tennican, "Antimicrobial Composition Including a Residual Barrier Film", 9 pages.

Office action for U.S. Appl. No. 13/688,044, dated Apr. 1, 2016, Tennican, "Port and Surface Cleaning Devices and Techniques", 10 pages.

Office Action for U.S. Appl. No. 13/688,044, dated May 28, 2015, Patrick O. Tennican, "Port and Surface Cleaning Devices and Techniques", 9 pages.

Office action for U.S. Appl. No. 13/688,044, dated Jun. 21, 2017, Tennican, "Port and Surface Cleaning Devices and Techniques", 9 pages.

Office action for U.S. Appl. No. 13/688,078, dated Jun. 29, 2017, Tennican, "Antimicrobial Composition Including a Residual Barrier Film", 13 pages.

Office action for U.S. Appl. No. 13/688,078, dated Jun. 3, 2016, Tennican, "Antimicrobial Composition Including a Residual Barrier Film", 8 pages.

Mexican Office Action dated Apr. 10, 2018 for Mexican patent application No. MX/a/2014/006413, a counterpart foreign application of U.S. Appl. No. 13/688,044, 6 pages.

Mexican Office Action dated Apr. 20, 2018 for Mexican patent application No. MX/a/2014/006414, a counterpart foreign application of U.S. Appl. No. 13/688,073, 6 pages.

Australian Office Action dated Mar. 2, 2017 for Australian Patent Application No. 2012346030, a counterpart foreign application of U.S. Appl. No. 13/688,073, 4 pages.

Chinese Office Action dated Mar. 16, 2018 for Chinese Patent Application No. 201280058307.6, a counterpart foreign application of U.S. Appl. No. 13/688,073, 11 pages.

European Office Action dated Jun. 21, 2018 for European patent application No. 12853916.0, a counterpart foreign application of U.S. Appl. No. 13/688,044, 5 pages.

Canadian Office Action dated Oct. 12, 2018 for Canadian patent application No. 2,856,534, a counterpart foreign application of U.S. Appl. No. 13/688,044, 6 pages.

Canadian Office Action dated Sep. 19, 2018 for Canadian patent application No. 2856539, a counterpart foreign application of U.S. Appl. No. 13/688,044, 6 pages.

* cited by examiner

CATHETER DEVICES AND TECHNIQUES

CROSS REFERENCE TO RELATED APPLICATION

This application claims priority to U.S. Provisional Patent Application No. 61/564,206 filed on Nov. 28, 2011, entitled "Medical Devices and Techniques for Antiseptic, Immunomodulatory and Antineoplastic Therapies," which is hereby incorporated by reference in its entirety.

BACKGROUND

Infection remains a real problem in the medical industry today. Infections are often caused by contamination of intravascular (IV) lines (e.g., intravenous, intra-arterial, etc.), contamination of an injection site or blood draw site (e.g., from a vein, artery, or capillary), urinary catheters, wound sites, incision sites, and numerous other sources of infection in healthcare facilities. For example, in the United States alone, central venous catheters cause an estimated 80,000 catheter-related blood stream infections per year, which result in up to 28,000 deaths among patients in intensive care units. O'Grady N P, Alexander M, Dellinger E P, et al., *Guidelines for the prevention of intravascular catheter-related infections*. MMWR Recomm Rep 2002; 51:1-29. These numbers do not include infections caused by contamination of injection sites, blood draw sites, catheters, or any of the other numerous sources of contamination in healthcare facilities. Infection is even more of a problem in developing nations, where syringes, IV lines, and other equipment are routinely used and re-used for multiple different patients.

BRIEF SUMMARY OF THE INVENTION

This application describes approaches to reducing and/or preventing infections. In one aspect, the application describes example antimicrobial compositions that may be used alone or in combination with catheters and catheter insertion sites. According to another aspect, the application describes catheters which may employ one or more protection devices, such as cleaning caps, protective caps or both. This summary is not intended to identify essential features of the claimed subject matter, nor should it be used to limit the scope of the claims.

A first embodiment of the invention concerns a catheter assembly comprising a package containing a catheter and at least one cleaning device. The cleaning device may be a cleaning cap, a protective cap or both. Moreover, the catheter may have at least one port.

Another embodiment concerns a method for obtaining a urine specimen comprising providing a catheter assembly, the catheter assembly comprising a package containing a catheter and at least one cleaning cap, wherein the catheter has at least one port; opening the package to remove the cleaning cap; installing the catheter at a urological catheter insertion site; cleaning said port with a port cleaning device; and obtaining a urine sample via the port. The catheter and at least one cleaning cap are individually sealed in separate compartments of the package.

Yet another embodiment concerns a method for administering an antimicrobial composition to a urological site comprising providing a catheter assembly, the catheter assembly comprising a package containing a catheter and at least one cleaning cap, wherein the catheter has at least one port; opening the package to remove the cleaning cap; installing a catheter at a urological catheter insertion site, said catheter having at least one port; cleaning said port with a port cleaning device; and administering an antimicrobial composition via the port. The catheter and at least one cleaning cap are individually sealed in separate compartments of the package.

DETAILED DESCRIPTION

Figure 1:
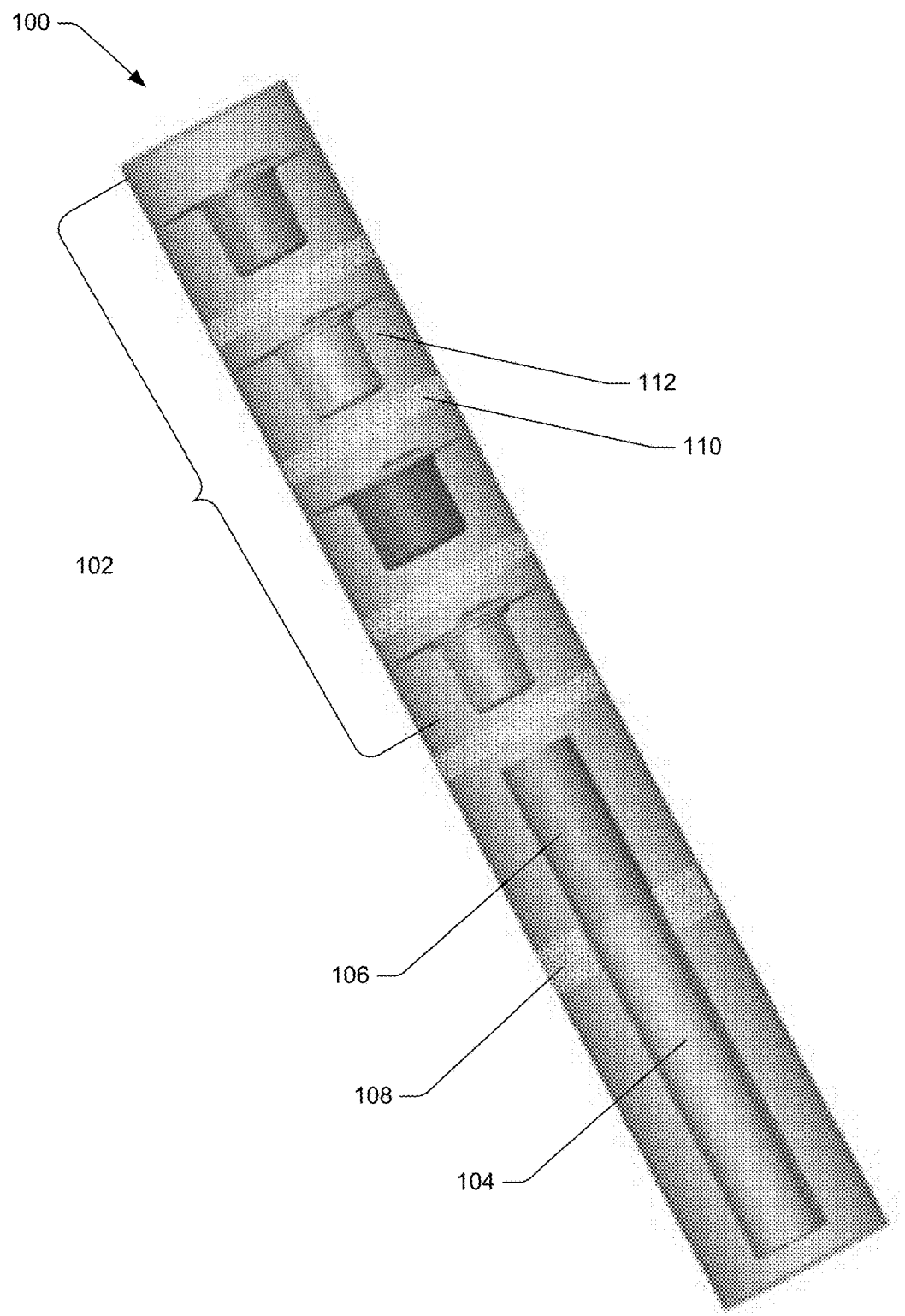
FIG. 1 shows a catheter assembly.

FIG. 1 illustrates an example of a catheter device and assembly which may, but need not necessarily, be used in connection with the antimicrobial compositions described herein. When used with the antimicrobial compositions described herein, however, the catheter device may provide disinfecting and/or therapeutic effects.

As shown in FIG. 1, a package 100 including one or more different site cleaning devices 102 coupled together with a catheter 104. The package 100 may comprise transparent, flexible, polymeric packaging allowing the user to see and inspect the contents of the package prior to use. The cleaning devices 102 and the catheter 104 may be individually sealed in separate compartments 112 of the package 100, wherein each compartment 112 is separated from an adjacent compartment 112 by a partition 110, or they may be sealed together in a common compartment 112 of the package. The cleaning devices 102 may be used to clean a catheter insertion site prior to insertion of the catheter 104. According to an embodiment, the cleaning device can be a piece of material such as a piece of cloth, swab, or sponge. According to an embodiment, the cleaning devices 102 may be cleaning caps, protective caps or both as further described below.

The catheter 104 may comprise a urinary catheter or any other type of catheter. In the case where the catheter 104 is a urinary catheter, the catheter may be either a Foley type, longer use, or a simple, straight, single use catheter. In either case, the catheter 104 would include an antimicrobial gel lubricant 106 applied to and/or contained at a tip area compartment of the package 100. The package 100 may include a restrictor 108 (e.g., a portion of the package fused closely to an exterior of the catheter midway along the length of the catheter) to prevent the gel lubricant from covering the whole exterior of the catheter 104. The one or more cleaning devices 102 being disposed in one or more compartments 112 ahead of the tip of the catheter 104, serve as a reminder to the user to clean and sanitize the catheter insertion site prior to insertion of the catheter. Once the site is cleaned, the catheter 104 may be inserted by peeling back the package 100 to expose the tip end of the catheter and holding the catheter via the package 100. In this way, the user need not even touch the catheter 104 during insertion, providing a "No Touch Cath" technique which even further reduces the risk of contamination and infection.

Additionally, in some embodiments, the lumen of the catheter 104 could be pre-filled with an antimicrobial composition such as those described herein.

Once the catheter 104 is installed, in some embodiments, the catheter may be used to obtain sterile, uncontaminated urine specimens via a urological catheter port. In that case, port cleaning and protection devices may be used to clean and protect the catheter port. The catheter port caps may use the same or different antimicrobial compositions than those used for the IV port cleaning and protective caps.

FIGS. 2A, 2B, and 3A-3C illustrate details of several example port cleaning and protective caps. Each of the caps may be made of materials such as, but not limited to, polyethylene, polypropylene, and/or copolymer materials. The caps may also comprise a material or agent that is UV protective to preserve the integrity of hydrogen peroxide during storage, shipping, etc. The caps themselves may additionally or alternatively be housed in a packaging that contains UV protective materials to inhibit breakdown of the hydrogen peroxide.

Figures 2A, 2B:
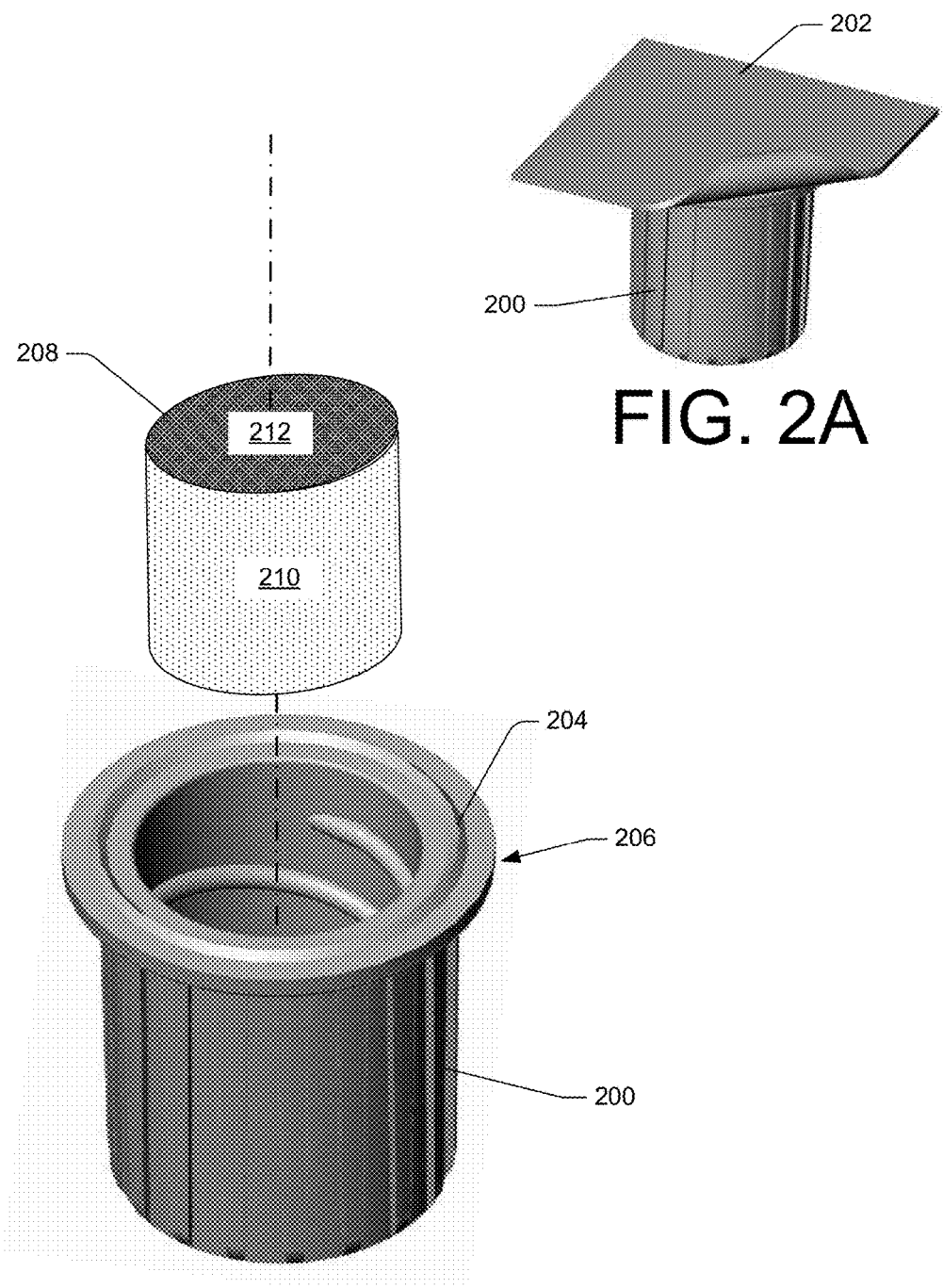
FIGS. 2A and 2B show details of an example cleaning device.

FIGS. 2A and 2B illustrate an example of an IV port protective cap 200 designed to thread onto a threaded port, such as a female Luer® connector, to provide a physical barrier against recontamination. As shown in FIG. 2A, the protective cap 200 is hermetically sealed by a protective cover 202. The protective cover 202 may be removably fused or bonded to the protective cap 200 by sonic welding, microwave welding, thermal fusion, or other bonding techniques. The protective cover 202 may be made of a same or different material than the protective cap 200. To facilitate the sealing of the protective cover 202 to the protective cap 200, as shown in FIG. 2B, the protective cap includes an energy director 204 disposed on a top surface of a rim 206 or flange surrounding an opening of the protective cap 200. The energy director 204 comprises a raised ridge or rib of material having a small cross section relative to the rim 206 of the protective cap 200. The small cross section of the energy director 204 allows the energy director to melt more quickly and to fuse with the protective cover 202 with less energy than that required to melt the entire rim 206 of the protective cap 200. The energy director 204 also allows the protective cover 202 to fuse to the protective cap 200 over a relatively thin region, thereby making the protective cover 202 easier to remove from the protective cap 200 than if it were fused over the entire area of the rim 206 of the protective cap 200.

The rim 206 is designed as a "no touch rim," which extends radially from the perimeter of the main body of the protective cap 200, thereby minimizing a likelihood that a user's fingers will come in contact with the internal surfaces of the protective cap during use. In the illustrated embodiment, the energy director 204 is disposed radially outward of an opening of the protective cap, but inward of an outer edge of the rim 206. This ensures that the portion of the rim 206 inside the energy director 204 remains sterile prior to use. The no touch rim 206 increases the likelihood that the portion of the rim 206 inside the energy director 204 remains sterile even during use. In other embodiments, the energy director may be disposed anywhere on the rim 206 (e.g., centrally as shown, at an inner perimeter of the rim proximate the opening, or at an outer perimeter of the rim).

As shown in FIG. 2B, the protective cap 200 also includes an applicator material 208 (shown in exploded view in this figure for clarity). In the illustrated example, the applicator material comprises a cylindrical foam material having an open cell region 210 around the circumference of the sides of the cylinder and a closed cell region 212 on one or both axial ends of the cylinder. The open cell region 210 allows the applicator material 208 to absorb and carry an antimicrobial composition, such as those described above. The closed cell region 212 serves to at least partially cover and seal an end of an IV port to prevent the IV port from leaking and to prevent substantial amounts of the antimicrobial composition from entering the IV port. Both the open cell region 210 and the closed cell region 212 may have a certain amount of texture or roughness to scrub the IV port.

Also, while applicator material 208 is illustrated as being a generally cylindrical body, in other embodiments, the applicator material may take on other shapes and/or sizes. Further, the applicator material 208 may include different surface treatments (e.g., siping, slitting, etc.), surface finishes (e.g., macro-, micro-, or nano-structures, etc.), and/or contours (e.g., rounded, ribbed, protrusions, fingers, etc.).

Figure 3A:
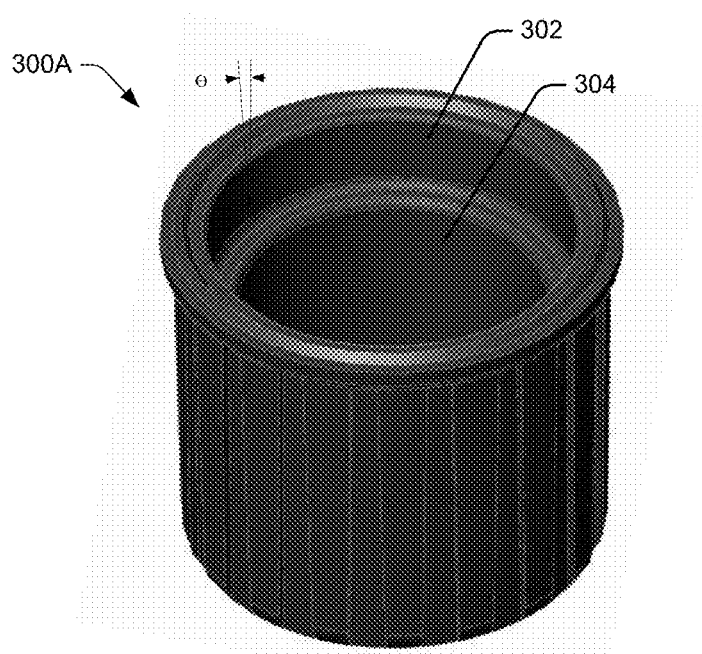
FIG. 3A-3C show details of several example cleaning devices.
Figure 3B:
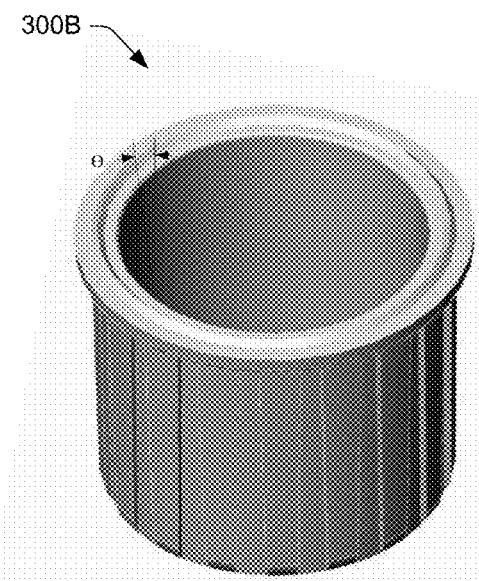
Figure 3C:
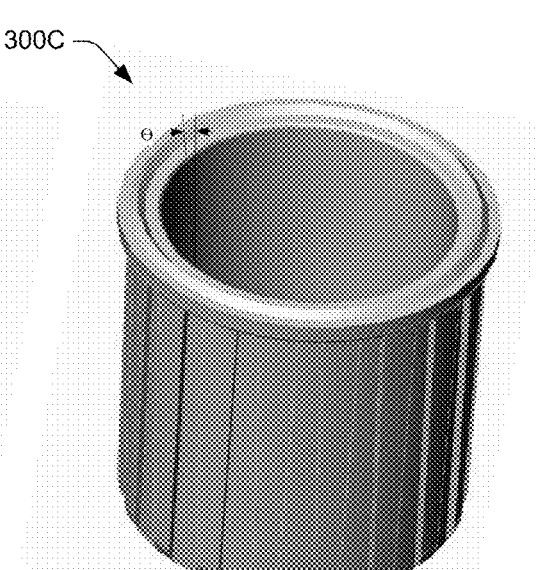

FIGS. 3A-3C illustrate several variations of IV port protective caps 300A, 300B, and 300C, respectively (collectively referred to as protective caps 300), for use with IV port connectors of varying outer diameter (OD), such as male Luer® connectors. The protective caps 300 of these embodiment are slip fit caps, in that they are designed to slip over and fit securely on IV port connectors of varying OD, since not all port connectors have standardize OD.

FIG. 3A illustrates a protective cap 300A having a stepped inner surface, including a first inner surface 302 and a second inner surface 304, the second inner surface 304 having a smaller average diameter than the first inner surface. The first and second inner surfaces 302 and 304 may have diameters chosen to match ODs of common ports on the market, of maximum and minimum ODs of ports on the market, or based on other criteria. Further both of the first and second inner surfaces 302 and 304 may be tapered (i.e., have a draft angle θ), such that a diameter of the first and second inner surfaces is largest closest to an opening of the protective cap 300A and decreases toward the bottom, closed end of the protective cap. A draft angle of the first inner surface 302 may be the same as, greater than, or less than a draft angle of the second inner surface 304. When the protective cap 300A is placed on an IV port, the protective cap 300A will slide over the IV port until an OD of the IV port contacts and seals against the interior surface of the protective cap 300A at either the first inner diameter 302 (in the case of an IV port with a relatively large OD) or the second inner diameter 304 (in the case of an IV port with a relatively small OD).

FIGS. 3B and 3C illustrate alternative embodiments of slip fit protective caps 300B and 300C, respectively, which have continuous, smooth inner surfaces. Rather than being stepped as in the embodiment of FIG. 3A, the protective caps 300B and 300C have continuous, smooth inner surfaces. Like the inner surfaces of the stepped protective cap 300, the inner surfaces of the protective caps 300B and 300C are tapered to accommodate IV ports of varying OD. However, in order to accommodate IV ports having a wide range of ODs, the draft angle θ of the protective caps needs to be larger (i.e., a more pronounced taper) as in the case of protective cap 300B, and/or the protective cap needs to be made deeper, as in the case of protective cap 300C.

Additional details of example IV port cleaning and protective devices may be found in U.S. patent application Ser. No. 11/745,843, filed May 8, 2007, to Tennican, which is incorporated herein by reference.

Additionally or alternatively, a flush syringe could be used to introduce a flush solution to flush the catheter lumen, bladder, ureter, renal pelvis, or other portions of the urinary tract. The flush solutions used may vary depending on the site to which it is to be delivered, e.g., catheter lumen, bladder, ureter, renal pelvis. In some examples, liquid antimicrobial compositions such as those described herein may be used as the flush solution.

According to an embodiment, the catheter assembly includes an antimicrobial composition. Exemplary antimicrobial compositions that may be used in connection with the approaches described herein may include those described in, for example, U.S. patent application Ser. No. 12/874,188, filed Sep. 1, 2010, to Tennican et al., which is incorporated herein by reference. In that case, the antimicrobial compositions may include water ($H_2O$), a strong and non-toxic chelating agent such as ethylenediaminetetraacetic acid (EDTA)(e.g., disodium EDTA, calcium disodium EDTA, magnesium EDTA, gallium EDTA) or sodium citrate (or acids, salts, derivatives, or other forms of EDTA or sodium citrate), a short-chain monohydric alcohol (e.g., ethanol with a molecular formula of $C_2H_5OH$ and an empirical formula of $C_2H_6O$), and a strong, small molecule oxidizing agent such as hydrogen peroxide ($H_2O_2$). In one specific example, the compositions may consist essentially of water, EDTA, ethanol, and hydrogen peroxide. However, in other examples, other antimicrobial compositions may be used in combination with the devices described in this application.

The antimicrobial compositions may be in a liquid form or a gel form, and may be combined with one or more carriers or diluents, depending on the needs of a specific application. For example, in applications in which the antimicrobial composition is used as a hand sanitizer, the antimicrobial composition may be in a gel. As another example, if the antimicrobial composition is used as a cleaning agent, a flush solution, or an irritant, the antimicrobial composition may be in a liquid form. In that case, the concentration of the various constituents may depend on, for example, a desired level of disinfection, whether the composition is being applied directly to living tissue or to a medical device, and/or to avoid irritation of tissue to which the composition will be applied directly or indirectly (e.g., via a medical device to which the composition is or was applied). In yet another example, the antimicrobial compositions may include or be combined with a lubricant (e.g., glycerin), surfactant or emulsifier (e.g., glycerol monolaurate (GML)), or the like and may be applied to a catheter, tracheal tube, scope, instrument, or other device that is to be inserted into a patient's body.

In other embodiments, for therapeutic treatment of localized infections and/or pre-malignant and malignant lesions in the urethra, bladder, ureter, renal pelvis, antimicrobial compositions such as those described herein may be delivered through a catheter or via direct observations via a cystoscope or ureteroscope or nephrostomy scope.

In still other embodiments, the antimicrobial compositions such as those described herein may be used as an irrigant to flush a catheter to prevent the buildup of biofilms and/or to break up the formation of stones.

Although the application describes embodiments having specific structural features and/or methodological acts, it is to be understood that the claims are not necessarily limited to the specific features or acts described. Rather, the specific features and acts are merely illustrative some embodiments that fall within the scope of the claims of the application.

What is claimed is:

1. A catheter assembly comprising:
    a single sealed package containing at least a first individually sealed compartment, a second individually sealed compartment, and a third individually sealed compartment, the respective individually sealed compartments separated from each other by partitions,
    wherein the first individually sealed compartment contains a catheter having a tip and at least one port,
    wherein the second individually sealed compartment contains a cleaning device used to clean a catheter insertion site prior to insertion of the catheter,
    wherein the third individually sealed compartment contains a protective cap,
    and
    wherein the second individually sealed compartment and the third individually sealed compartment are disposed ahead of and adjacent to the tip of the catheter.

2. The catheter assembly according to claim 1, wherein the package is transparent.

3. The catheter assembly according to claim 1, wherein the catheter is a urinary catheter.

4. The catheter assembly according to claim 1, wherein the package further includes an antimicrobial gel lubricant applied to and/or contained in proximity to the tip of the catheter.

5. The catheter assembly according to claim 4, wherein a portion of the package is fused closely to an exterior of the catheter midway along the length of the catheter to prevent the antimicrobial gel lubricant from migrating away from the tip and covering another area of the catheter.

6. The catheter assembly according to claim 1, wherein at least a portion of an inside of the catheter contains an antimicrobial composition.

7. The catheter assembly according to claim 1, further comprising an applicator material.

8. The catheter assembly according to claim 7, wherein the applicator material includes an antimicrobial composition.

9. A method for using a catheter comprising:
    obtaining a catheter assembly, the catheter assembly comprising a single sealed package containing a catheter having a tip and at least one port, a cleaning device, and a port cleaning cap, wherein the catheter, the cleaning device, and the port cleaning cap are individually sealed in separate compartments of the package and each of the separate compartments is separated from an adjacent compartment by a partition;
    opening the package to remove the cleaning device;
    cleaning the catheter insertion site with the cleaning device;
    installing the catheter at the catheter insertion site;
    opening the package to remove the port cleaning cap; and
    cleaning said port with the port cleaning cap.

10. The method according to claim 9, wherein the package also contains at least one protective cap and the method further comprising covering the port with the protective cap.

11. The method according to claim 9, wherein the package further includes an antimicrobial gel lubricant applied to and/or contained in proximity to the tip of the catheter.

12. The method according to claim 11, wherein a portion of the package is fused closely to an exterior of the catheter midway along the length of the catheter to prevent the antimicrobial gel lubricant from migrating away from the tip area and covering another area of the catheter.

13. The method according to claim 9, further comprising an applicator material contained within the port cleaning cap.

14. The method according to claim 13, wherein the applicator material includes an antimicrobial composition.

15. The method according to claim 9, further comprising obtaining a sample via the port.

16. The method according to claim 9, wherein catheter assembly is configured with the separate compartment containing the cleaning device and the separate compartment containing the port cleaning cap disposed ahead of and adjacent to the tip of the catheter.

17. A catheter assembly comprising a single sealed package containing a catheter and a plurality of cleaning devices, wherein the plurality of cleaning devices include at least two of: a cleaning device used to clean a catheter insertion site prior to insertion of the catheter, a port cleaning cap, or a protective cap, wherein the catheter and each of the cleaning devices are individually sealed in separate compartments of the package and said cleaning devices are disposed in the separate compartments ahead of and adjacent to a tip of the catheter, and wherein each separate compartment is separated from an adjacent compartment by a partition.

18. The catheter assembly according to claim 17, further comprising an applicator material contained within the port cleaning cap.

19. The catheter assembly according to claim 18, wherein the applicator material includes an antimicrobial composition.

20. The catheter assembly according to claim 19, wherein the antimicrobial composition comprises water, a chelating agent, a short-chain monohydric alcohol, and hydrogen peroxide.

* * * * *